US00PP11036P

United States Patent [19]

Olij

[11] Patent Number: Plant 11,036

[45] Date of Patent: Aug. 17, 1999

[54] HYBRID TEA ROSE PLANT NAMED 'OLIJSAB'

[75] Inventor: Huibert W. Olij, De Kwakel, Netherlands

[73] Assignee: Olij Rozen B.V., de Kwakel, Netherlands

[21] Appl. No.: 09/038,282

[22] Filed: Mar. 11, 1998

[51] Int. Cl.[6] ..... A01H 5/00

[52] U.S. Cl. ..... Plt./130

[58] Field of Search ..... Plt./130, 135, 136, Plt./137

*Primary Examiner*—Howard J. Locker

*Attorney, Agent, or Firm*—Burns, Doane, Swecker & Mathis, L.L.P.

[57] ABSTRACT

A new and distinct variety of Hybrid Tea rose plant is provided which forms attractive orange-red blossoms which exhibit a long vase life. The buds are long, and are borne on long erect stems. Attractive semi-glossy foliage is formed, and the plant exhibits good disease resistance. The new variety is particularly well suited for producing cut flowers under greenhouse growing conditions.

1 Drawing Sheet

SUMMARY OF THE INVENTION

The new variety of Hybrid Tea rose plant was created by artificial pollination wherein two parents were crossed which previously had been studied in the hope that they would contribute the desired characteristics. The female parent (i.e., the seed parent) of the new variety was the 'Keizoubo' variety (U.S. Plant Pat. No. 8,024). The male parent (i.e., the pollen parent) was the 'Meivamo' variety (U.S. Plant Pat. No. 8,619). The parentage of the new variety can be summarized as follows:

('Keizoubo'×'Meivamo').

The seeds resulting from the above pollination were sown and 14 small plants were obtained which were physically and biologically different from each other. Selective study resulted in the identification of a single plant of the new variety.

It was found that the new variety of Hybrid Tea rose plant of the present invention possesses the following combination of characteristics:

(a) forms attractive elongated buds on long and erect stems,
(b) forms in abundance attractive orange-red blossoms which exhibit a long vase life,
(c) forms attractive semi-glossy foliage,
(d) exhibits good disease resistance, and
(e) is particularly well suited for the production of cut flowers under greenhouse growing conditions.

The new variety well meets the needs of the horticultural industry and exhibits good productivity during cut flower production in a greenhouse.

The new variety has been found to undergo asexual propagation in France by a number of routes, including budding, grafting, and cuttage. Asexual propagation by the above-mentioned techniques in France has shown that the characteristics of the new variety are stable and are strictly transmissible by such asexual propagation from one generation to another.

The new variety has been named the 'Olijsab' variety.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety were two years of age and were observed during April while budded on *Rosa indica* understock and growing in greenhouses at Le Cannet des Maures, Var, France. Dimensions in centimeters are indicated at the bottom of the photograph. Page No. 35 from The R.H.S. Colour Chart of The Royal Horticultural Society is shown at the lower-left portion of the photograph for comparative purposes.

DETAILED DESCRIPTION

Figures 1, 2, 3, 4, 5, 6, 7, 8, 9, 10, 11, 12, 13, 14, 15, 16:
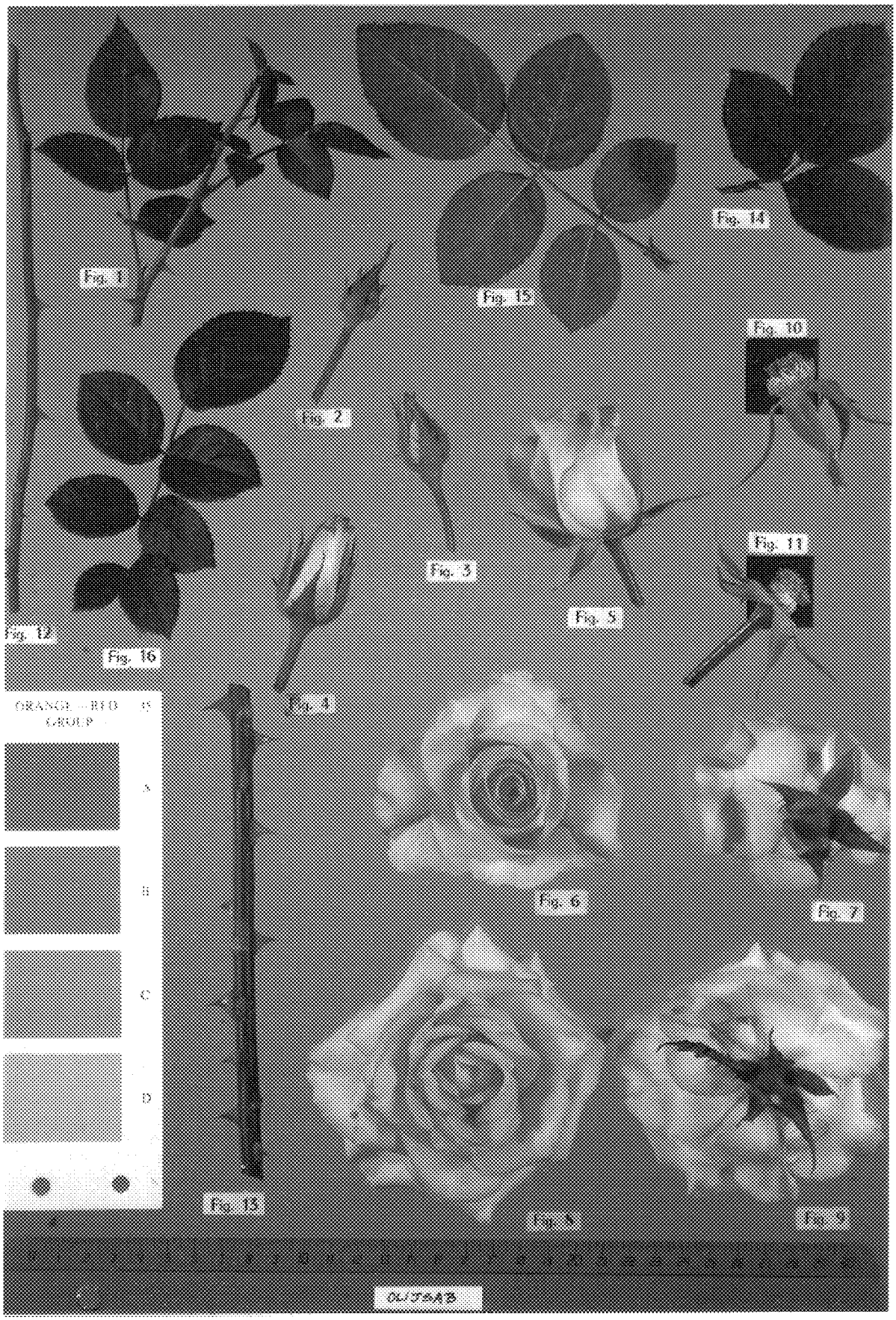
FIG. 1 illustrates a specimen of a young shoot.
FIG. 2 illustrates a specimen of a floral bud before the opening of the sepals.
FIG. 3 illustrates a specimen of a floral bud at the opening of the sepals.
FIG. 4 illustrates a specimen of a floral bud at the opening of the petals.
FIG. 5 illustrates a specimen of a flower in the course of opening.
FIG. 6 illustrates a specimen of an open flower—plan view—obverse.
FIG. 7 illustrates a specimen of an open flower—plan view—reverse.
FIG. 8 illustrates a specimen of a fully open flower—plan view—obverse.
FIG. 9 illustrates a specimen of a fully open flower—plan view—reverse.
FIG. 10 illustrates a specimen of a floral receptacle showing the arrangement of the stamens and pistils.
FIG. 11 illustrates a specimen of a floral receptacle showing the arrangement of the pistils (stamens removed)
FIG. 12 illustrates a specimen of a flowering stem.
FIG. 13 illustrates a specimen of a main branch.
FIG. 14 illustrates a specimen of a leaf with three leaflets—plan view—upper surface.
FIG. 15 illustrates a specimen of a leaf with five leaflets—plan view—under surface.
FIG. 16 illustrates a specimen of a leaf with seven leaflets—plan view—upper surface.

The chart used in the identification of the colors is that of The Royal Horticultural Society (R.H.S. Colour Chart). The description is based on the observation of two- year-old plants during November while budded on *Rosa indica* understock and growing indoors at Le Cannet des Maures, Var, France. The coloration in common terms precedes reference to the chart in some instances.

Class: Hybrid Tea.

Plant:

*Height.*—When pruned to a height of 85 cm., floral stems of approximately 70 to 90 cm. in length commonly are produced.

*Habit.*—Erect.

Branches:

*Color.*—Young stems: Yellow-Green Group 146C in coloration. Adult wood: Yellow-Green Group 146B in coloration.

*Thorns.*—Size: large (as illustrated). Quantity: moderately numerous. Color: greenish on young stems and Havana brown on adult wood.

Leaves:

*Stipules.*—Adnate, pectinate, narrow and linear.

*Petioles.*—Upper surface: striped reddish-brown on young foliage, and medium green on adult foliage and less glandular. Under surface: medium green, and rarely bear small thorns.

*Leaflets.*—Number: 3, 5 (most often), and 7. Shape: oval. Serration: single and regular (as illustrated). Texture: consistent. General appearance: dense, medium green, and semi-glossy. Color (young foliage): Upper surface: near Yellow-Green Group 137B. Under surface: near Yellow-Green Group 137C. Color (adult foliage): Upper surface: near Yellow-Green Group 137A. Under surface: near Yellow-Green Group 138B.

Inflorescence:

*Number of flowers.*—Usually one flower per stem, and may have up to about three flowers per stem.

*Peduncle.*—Medium green in coloration, bears a few prickles, and the length is approximately 10 cm. on average.

*Sepals.*—Upper surface: tomentose and greenish in coloration. Under surface: light green in coloration and commonly with some extensions (as illustrated).

*Buds.*—Shape: elongated. Size: medium to large. Length: approximately 4 cm. on average. Color upon opening: Upper surface: near Orange Group 25B with some greenish veins. Under surface: near Orange Group 26C with some greenish veins.

*Flower.*—Shape: umbrella-shaped. Diameter: commonly approximately 12 cm. on average. Color (when opening begins): Upper surface: near Yellow-Orange Group 21B at the base and suffused with Red Group 37C at the center and towards the opposite end of the petal. Under surface: near Greyed-Orange Group 163C at the base and widely suffused with Red Group 36B at the opposite end of the petal. There commonly is a light petal edge of Orange-Red Group 35C. Color (when blooming): Upper surface: near Orange Group 25C at the base and suffused with Orange-Red Group 35D at the opposite end. Under surface: near Yellow-Orange Group 15D at the base and widely suffused with Orange Group 27C at the opposite end. The petal commonly is lightly edged with Orange-Red Group 35C. Color (at end of opening): Upper surface: near Yellow-Orange Group 23C at the base and suffused with Orange Group 26D at the opposite end. Under surface: near Yellow-Orange Group 18B at the base, near Orange Group 29D towards the center of the petal, and lightly edged with Orange-Red Group 35C. Fragrance: slight. Lasting quality: very good, approximately 7 to 9 days on the plant and approximately 8 to 10 days when cut and placed in a vase. Petal shape: rounded with reflexed edges. Petal drop: good, the petals commonly detach cleanly. Stamen number: approximately 110 on average. Anthers: normal and golden yellow in coloration. Filaments: yellowish in coloration. Pistils: approximately 150 on average. Stigmas: yellowish in coloration. Styles: greenish/yellowish in coloration. Receptacle: light green in coloration, smooth, and in longitudinal section in the shape of a pitcher.

Development:

*Vegetation.*—Vigorous.

*Blooming.*—Abundant, and commonly produces 130 to 150 flowers/m.$^2$/year.

*Resistance to diseases.*—Very good.

I claim:

1. A new and distinct variety of Hybrid Tea rose plant characterized by the following combination of characteristics:

(a) forms attractive elongated buds on long and erect stems,
(b) forms in abundance attractive orange-red blossoms which exhibit a long vase life,
(c) forms attractive semi-glossy foliage,
(d) exhibits good disease resistance, and
(e) is particularly well suited for the production of cut flowers under greenhouse growing conditions;

substantially as herein shown and described.

* * * * *

ORANGE—RED GROUP
A
B
C
D